(12) United States Patent
Höpfner et al.

(10) Patent No.: US 9,868,750 B2
(45) Date of Patent: Jan. 16, 2018

(54) 4,5-DIARYLIMIDAZOLE DERIVATIVES AS HDAC INHIBITORS

(71) Applicants: CHARITÉ—UNIVERSITÄTSMEDIZIN BERLIN, Berlin (DE); UNIVERSITÄT BAYREUTH, Bayreuth (DE); Michael Höpfner, Berlin (DE); Bernhard Biersack, Prebitz (DE); Rainer Schobert, Bayreuth (DE); Katharina Mahal, Bayreuth (DE)

(72) Inventors: Michael Höpfner, Berlin (DE); Bernhard Biersack, Prebitz (DE); Rainer Schobert, Bayreuth (DE); Katharina Mahal, Bayreuth (DE)

(73) Assignees: CHARITÉ—UNIVERSITÄTSMEDIZIN BERLIN, Berlin (DE); UNIVERSITÄT BAYREUTH, Bayreuth (DE)

( * ) Notice: Subject to any disclaimer, the term of this patent is extended or adjusted under 35 U.S.C. 154(b) by 0 days.

(21) Appl. No.: 15/326,381

(22) PCT Filed: Jul. 13, 2015

(86) PCT No.: PCT/EP2015/065948
§ 371 (c)(1),
(2) Date: Jan. 13, 2017

(87) PCT Pub. No.: WO2016/008836
PCT Pub. Date: Jan. 21, 2016

(65) Prior Publication Data
US 2017/0197992 A1 Jul. 13, 2017

(30) Foreign Application Priority Data
Jul. 18, 2014 (EP) .................................... 14177580

(51) Int. Cl.
*C07F 1/00* (2006.01)
*C07D 233/64* (2006.01)

(52) U.S. Cl.
CPC .............. *C07F 1/00* (2013.01); *C07D 233/64* (2013.01)

(58) Field of Classification Search
CPC ................................ C07D 233/64; C07F 1/00
(Continued)

(56) References Cited

FOREIGN PATENT DOCUMENTS

| WO | WO 2004/063169 A1 | 7/2004 |
| WO | WO 2005/065681 A1 | 7/2005 |
| WO | WO 2011/138409 A1 | 11/2011 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Dignam, et al., "Accurate transcription initiation by RNA polymerase II in a soluble extract from isolated mammalian nuclei," Nucleic Acids Research, vol. 11, Issue 5, 1983, pp. 1475-1489.
(Continued)

*Primary Examiner* — Kristin Vajda
(74) *Attorney, Agent, or Firm* — Lewis Roca Rothengerber Christie LLP

(57) ABSTRACT

The present invention relates to a 4,5-diarylimidazole derivative of formulae (I), (II) or (III): or a pharmaceutically acceptable salt thereof, wherein the 4,5-diarylimidazole derivative has a hydroxamic acid residue at a first aryl ring and a residue R1 at a second aryl ring; and wherein R1 is hydrogen, a halogen atom or an unsubstituted or substituted alkoxy group; R2 is independently selected from an unsubstituted or substituted alkyl, alkoxy or alkene group; M is a metal atom; L is a halogen atom, an unsubstituted or substituted phosphane, sulfane, arene or alkene group or a 4,5-diarylimidazole-derivative of formula (I); and n is an integer of from 1 to 5.

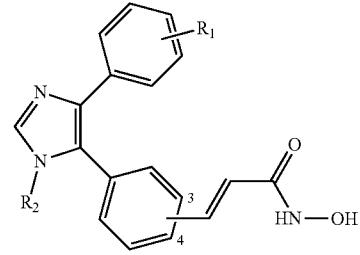

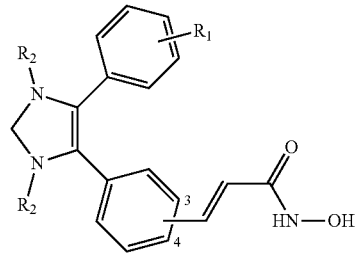

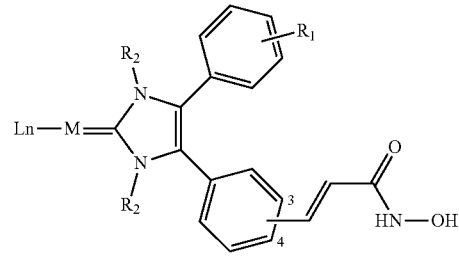

11 Claims, 9 Drawing Sheets

Figure 1:
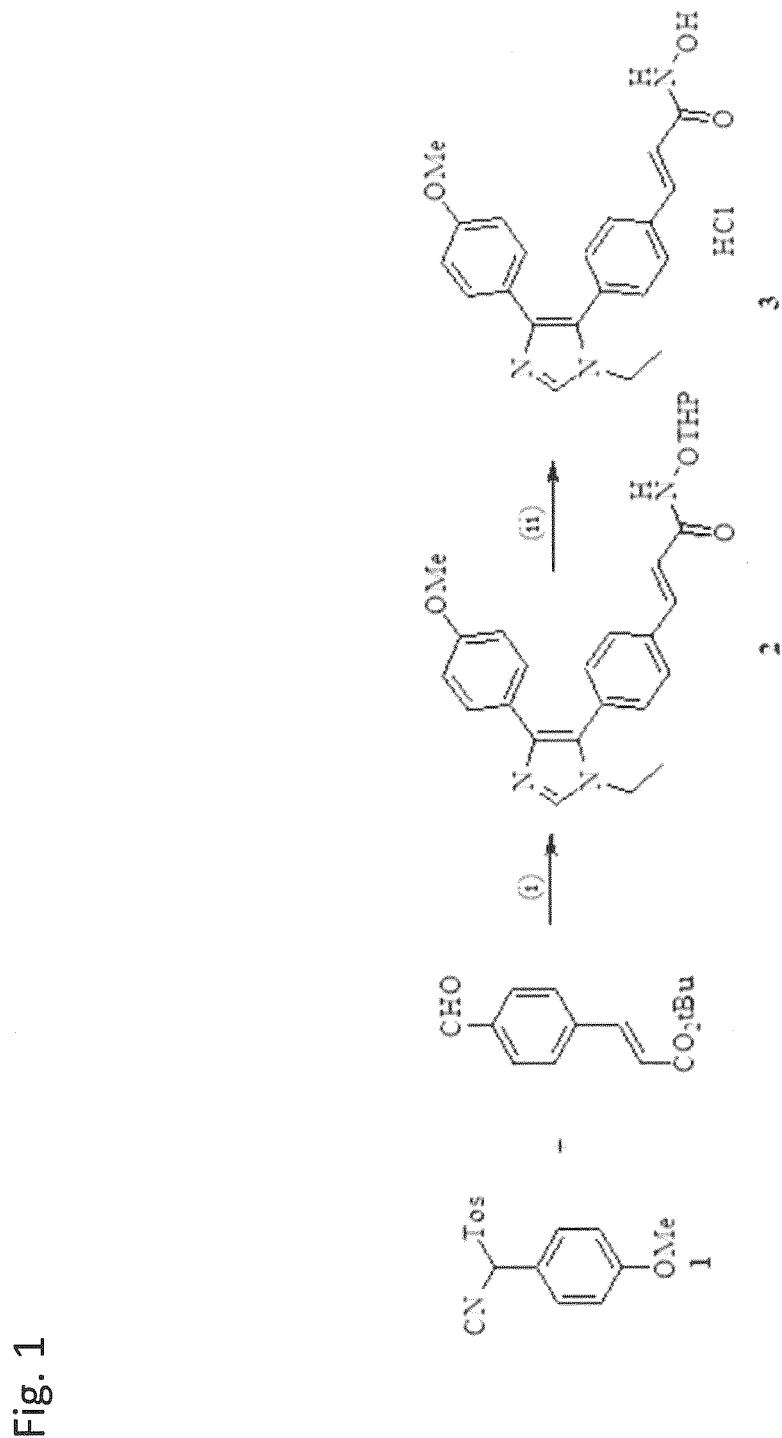

(58) Field of Classification Search
USPC .......................................................... 514/184
See application file for complete search history.

(56) References Cited

OTHER PUBLICATIONS

Bressi et al., "Benzimidazole and imidazole inhibitors of histone deacetylases: Synthesis and biological activity," Bioorganic & Medicinal Chemistry Letters, vol. 20, 2010, pp. 3138-3141.

Wang et al., "Potent, Orally Active Heterocycle-Based Combretastatin A-4 Analogues: Synthesis, Structure-Activity Relationship, Pharmacokinetics, and In Vivo Antitumor Activity Evaluation," Journal of Medicinal Chemistry, vol. 45, Issue 8, 2002, pp. 1697-1711.

Xiang et al., "Pharmacophore and QSAR Studies to Design Novel Histone Deacetylase 2 Inhibitors," Chemical Biology and Drug Design, vol. 79, 2012, pp. 760-770.

* cited by examiner

4,5-DIARYLIMIDAZOLE DERIVATIVES AS HDAC INHIBITORS

CROSS-REFERENCED TO RELATED APPLICATION(S)

This application is a US national phase application of International Patent Application No. PCT/EP2015/065948, filed Jul. 13, 2015 and claiming the priority of European Patent Application No. 14177580.9, filed Jul. 18, 2014, the entire contents of each of which are hereby incorporated herein by reference.

DNA in eukaryotic cells is tightly complexed with proteins, e.g. histones, to form chromatin. Histones are small positively charged proteins that are rich in basic amino acids which contact the phosphate groups of DNA. There are five main classes of histones H1, H2A, H2B, H3 and H4. The amino acid sequences of H2A, H2B, H3 and H4 show remarkable conservation between species, wherein H1 varies somewhat and in some cases is replaced by another histone, e.g. H5. Four pairs of each of H2A, H2B, H3 and H4 together form a disk-shaped octomeric protein core, around which DNA is wound to form a nucleosome. Individual nucleosomes are connected by short stretches of linker DNA associated with another histone molecule to form a structure resembling a beaded string, which itself is arranged in a helical stack known as a solenoid.

A small fraction of histones, more specifically the amino acid side chains thereof, are enzymatically modified by post-translational addition of methyl, acetyl or phosphate groups, neutralizing the positive charge of the side chain or converting it into a negative charge. For example, lysine and arginine groups may be methylated, lysine groups may be acetylated and serine groups may be phosphorylated. Methylation, acetylation and phosphorylation of amino acid termini of histones affect the chromatin structure and gene expression.

Acetylation and deacetylation of histones is associated with transcriptional events leading to cell proliferation and/or differentiation. Certain enzymes, specifically acetylases like histone acetyltransferases (HATs) and histone deacetylases (HDACs) which regulate the acetylation state of histones have been identified in many organisms and have been implicated in the regulation of numerous genes, confirming a link between acetylation and transcription. In general, histone acetylation is believed to correlate with transcriptional activation, whereas histone deacetylation is believed to be associated with gene repression.

Studies of HDAC inhibitors have shown that these enzymes play an important role in cell proliferation and differentiation. HDACs are believed to be associated with a variety of different disease states including cell proliferative diseases and conditions such as leukemia, melanomas or squamous cell carcinomas, breast cancer, prostate cancer, bladder cancer, lung cancer, ovarian cancer and colon cancer.

HDAC inhibitors are potent inducers of growth arrest, differentiation or apoptotic cell death in a variety of transformed cells in culture and in tumor bearing animals. In addition, HDAC inhibitors are useful in the treatment or prevention of protozoal diseases and psoriasis.

Several natural and synthetic compounds that inhibit HDACs are currently known. Since HDAC inhibitors do not inhibit all HDAC isoforms to the same extent, they can be categorized into pan- and class-specific inhibitors. Hydroxamic acids like SAHA (vorinostat), trichostatin A (TSA), LAQ824 (dacinostat), m-carboxycinnamic acid bis-hydroxamide (CBHA), PCI24781, LBH589 (panobinostat) and pyroxamic acids like PXD101 (belinostat) and CRA-026440 are pan-HDAC inhibitors targeting class I, II and IV HDACs. In contrast, carboxylic acids like valroic acid or butyrate and benzamides like MS275 (entinostat), acetyl-dinaline (CI-994) or MGCD0103 (mocetinostat) as well as cyclic tetrapeptides like FK228 (romidepsin), trapoxin, depsipeptide and spiruchostatin A are rather class I-specific inhibitors.

Despite the diverse HDAC inhibitors that have been reported to date, new and more effective HDAC inhibitors are needed.

It is an object of the present invention to provide alternatives to known HDAC inhibitors.

The present invention relates to 4,5-diarylimidazole derivatives or pharmaceutically acceptable salts thereof as compounds that have activity for inhibiting HDACs.

As used in this specification and the appended claims, the singular forms "a", "an" and "the" include singular and plural referents unless the content clearly dictates otherwise. Thus, for example, reference to "a 4,5-diarylimidazole derivative" includes one 4,5-diarylimidazole derivative and a combination of two or more 4,5-diarylimidazole derivatives and the like.

According to the invention, the 4,5-diarylimidazole derivatives are compounds of formulae (I), (II) or (III) or pharmaceutically acceptable salts thereof:

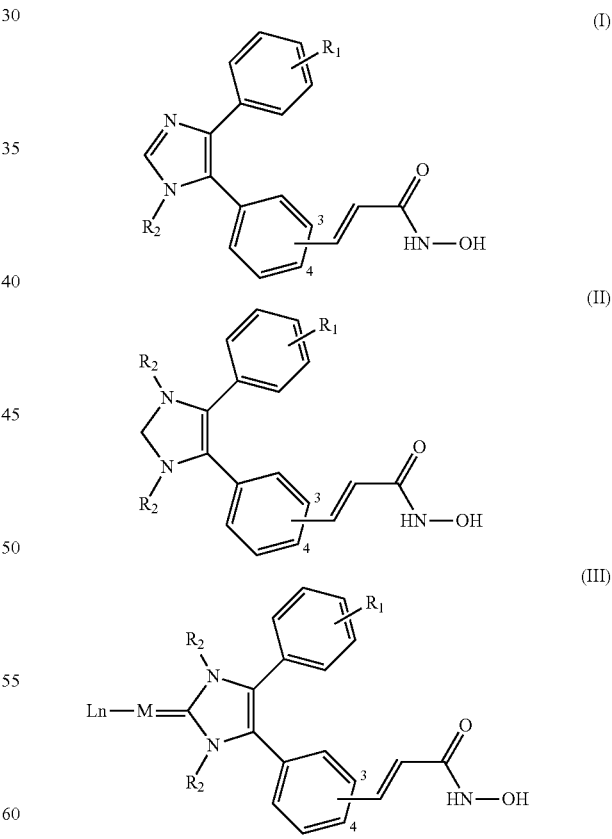

wherein the 4,5-diarylimidazole derivative has a hydroxamic acid residue at a first aryl ring and a residue R1 at a second aryl ring; and wherein R1 is hydrogen, a halogen atom or an unsubstituted or substituted alkoxy group;

R2 is independently selected from an unsubstituted or substituted alkyl, alkoxy or alkene group;

M is a metal atom;

L is a halogen atom, an unsubstituted or substituted phosphane, sulfane, arene or alkene group or a 4,5-diarylimidazole-derivative of formula (I); and n is an integer of from 1 to 5.

In the present invention, the term "derivative" is intended to mean a compound that is derived from a parent compound by some chemical or physical process. Derivatives are compounds whose molecules have, instead of a hydrogen atom or a functional chemical group at a certain position in the parent compound, another atom or another functional chemical group, or in which one or more atoms or functional chemical groups have been removed respectively.

The 4,5-diarylimidazole derivatives of the present invention may be in the form of a pharmaceutically acceptable salt. As used herein, the term "pharmaceutically acceptable salt" includes acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). When the compounds of the present invention possess a free base form, the compounds can be prepared as a pharmaceutically acceptable acid addition salt by reacting the free base form of the compound with a pharmaceutically acceptable inorganic or organic acid, e.g. hydrohalides such as hydrochloride, hydrobromide, hydroiodide; other mineral acids and their corresponding salts such as sulfate, nitrate, phosphate, etc.; and alkyl- and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include adipate, alginate, arginate, aspartate, benxenesulfonate (hesylate), bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, ethanesulfonate, fumarate, galacterate (from mucic acid), galacturonate, glucoheptaoate, glucorrate, glutamate, glycerophosplrate, hemisuecinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include copper, ferric, ferrous, lithium, magnesium, manganic, manganous, potassium, sodium and zinc salts. Organic base salts include salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, diethylamine, 2-diethylaminoethanol, Z-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamirre, trimethylamine, tripropylamine and tris-(hydroxymethyl)-methylamine (tromethamine). Preferably, the pharmaceutically acceptable salt form of the 4,5-diarylimidazole derivatives is a hydrochloride salt or a AuCl complex.

Salts may also be prepared by exchanging a counter-ion of a compound of the invention in the form of a salt with another counter-ion, for example using a suitable ion exchange resin. The salt form may confer improved pharmacokinetic properties on the 4,5-diarylimidazole derivative as compared to the free form of the compound. The pharmaceutically acceptable salt form may also positively affect the pharmacodynamics of the compound with respect to its therapeutic activity in the body. An example of pharmacodynamics property that may be favorably affected is the manner in which the compound is transported across cell membranes, which in turn may directly and positively affect the adsorption, distribution, biotransformation and excretion of the compound.

As used herein, the term "hydroxamic acid" denotes organic compounds having the functional group RC(O)N(OH)R', with R and R' as organic residues and CO as a carbonyl group. They are amides (RC(O)NHR') in which the hydrogen atom has been replaced by a hydroxyl group.

As used herein, "halogen atom" means fluorine, chlorine, bromine and iodine atoms. Fluorine atoms are preferred.

In the present invention, "substituted or unsubstituted" means that a given moiety may consists of only hydrogen substituents through available valencies (unsubstituted) or may further comprise one or more non-hydrogen substituents through available valencies (substituted) that are not otherwise specified by the name of the given moiety. In general, a non-hydrogen substituent may be any substituent that may be bound to an atom of the given moiety that is specified to be substituted. Examples of substituents are aldehyde, alicyclic, aliphatic, alkyl, alkylene, alkylidene, amide, amino, aminoalkyl, aromatic, aryl, bicycloalkyl, bicycloaryl, carbamoyl, carbocycle, carboxy, carbonyl group, cycloalkyl, cycloalkylene, ester, halogen, heterobicycloalkyl, heterocycloalkylene, heteroaryl, heterobicycloaryl, heterocycloalkyl, hydroxy, iminoketone, ketone, nitro, oxaalkyl and oxaalkyl moieties, each of which may optionally also be substituted or unsubstituted. "Aryl" means a carboxylic aromatic group containing one or more rings, e.g. one, two or three rings, wherein such rings may be attached together in a pendent manner, such as biphenyl or may be fused, such as naphthalene. Examples include phenyl, naphthyl, thienyl, indolyl etc. Preferably, the aryl group is phenyl. The term "aromatic" means a carbocycle, i.e. the ring atoms are only carbon atoms, or heterocycle, i.e. the ring atoms include carbon and non-carbon atoms, having on or more polyunsaturated rings with aromatic character, wherein all atoms in the ring system are sp2 hybridized and the total number of pi electrons is equal to 4n+2.

As used herein, the term "alkoxy" means an oxygen moiety having a further alkyl substituent. "Alkyl" means a straight or branched, saturated or unsaturated, aliphatic radical having a chain of carbon atoms, optionally with oxygen (oxaalkyl) or nitrogen atoms (aminoalkyl) between the carbon atoms. Notations like $C_x$ alkyl and $C_{x-y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2methylallyl, ethynyl, 1-propynyl, 2-propynyl, and the like). Preferably, the alkoxy group is methoxy.

As used herein, the term "phosphane" is intended to mean phosphorated hydrogens with the general formula $P_nH_{n+2}$.

As used herein, "sulfane" means hydrogen sulfide.

In the present invention, the term "arene" means aromatic hydrocarbons with alternating double and single bonds between the ring forming carbon atoms. Aromatic hydrocarbons can be monocylic or polycyclic.

The term "alkene" is used to describe unsaturated hydrocarbons containing at least one carbon-carbon double bond. The simplest acyclic alkenes, with only one double bond and no other functional groups, known as mono-enes, form a homologous series of hydrocarbons with the general formula $C_nH_{2n}$.

According to the invention, the 4,5-diarylimidazole derivatives are compounds of formulae (I), (II) or (III) or pharmaceutically acceptable salts thereof, wherein R1 is a hydrogen, a halogen atom or a $C_{1-4}$ alkoxy group. Preferably, R1 is a hydrogen, a halogen atom or a methoxy or ethoxy group, more preferably R1 is a hydrogen, a fluorine atom or a methoxy group and most preferably R1 is a hydrogen or a methoxy group. Preferably, R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein R2 is a $C_{1-4}$ alkyl group. Preferably R2 is a methyl or ethyl group.

According to the invention, the 4,5-diarylimidazole derivatives are compounds of formula (III) or pharmaceutically acceptable salts thereof, wherein M is a transition metal atom. Preferably M is Cu, Ag, Au, Rh, Ir, Pt or Ru, more preferably M is Au.

According to the invention, the 4,5-diarylimidazole derivatives are compounds of formula (III) or pharmaceutically acceptable salts thereof, wherein L is a $P_{1-4}$ phosphane, sulfane, arene or alkene group or the 4,5-diarylimidazole derivative according to formula (I). Preferably L is the 4,5-diarylimidazole derivative according to formula (I).

According to the invention, the 4,5-diarylimidazole derivatives are compounds of formula(III) or pharmaceutically acceptable salts thereof, wherein n is an integer of from 1 to 3. Preferably n is an integer of from 1 to 2, more preferably n is 1.

According to the invention, the 4,5-diarylimidazole derivatives are compounds of formulae (I), (II) or (III) or pharmaceutically acceptable salts thereof, wherein the hydroxamic acid is preferably at position 3 or 4 of the first aryl ring.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or an unsubstituted or substituted alkoxy group, R2 is independently selected from an unsubstituted or substituted alkyl, alkoxy or alkene group, M of formula (III) is a metal atom, L of formula (III) is a halogen atom, an unsubstituted or substituted phosphane, sulfane, arene or alkene group or a 4,5-diarylimidazole-derivative of formula (I) and n of formula (III) is an integer of from 1 to 5. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a $C_{1-4}$ alkoxy group, R2 is a $C_{1-4}$ alkyl group, M of formula (III) is a transition metal atom, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a methyl or ethyl group, M of formula (III) is Cu, Ag, Au, Rh, Ir, Pt or Ru, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a $C_{1-4}$ alkoxy group, R2 is a methyl or ethyl group, M of formula (III) is a metal atom, L of formula (III) is a P1-4 phosphane, sulfane, arene or alkene group or the 4,5-diarylimidazole derivative according to formula (I) and n of formula (III) is an integer of from 1 to 5. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a $C_{1-4}$ alkoxy group, R2 is a methyl or ethyl group, M of formula (III) is a metal atom, L of formula (III) is a $P_{1-4}$ phosphane, sulfane, arene or alkene group or the 4,5-diarylimidazole derivative according to formula (I) and n of formula (III) is an integer of from 1 to 3. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5- diarylimidazole derivatives have a hydroxamic acid residue at a first aryl ring and a residue R1 at a second aryl ring and wherein R1 is a hydrogen, a halogen atom or a $C_{1-4}$ alkoxy group, R2 is a methyl or ethyl group, M of formula (III) is a metal atom, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a $C_{1-4}$ alkyl group, M of formula (III) is a metal atom, L of formula (III) is a $P_{1-4}$ phosphane, sulfane, arene or alkene group or the 4,5-diarylimidazole derivative according to formula (I) and n of formula (III) is an integer of from 1 to 3. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a $C_{1-4}$ alkyl group, M of formula (III) is a metal atom, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a fluorine atom or a methoxy group, R2 is a $C_{1-4}$ alkyl group, M of formula (III) is a metal atom, L of formula (III) is a $P_{1-4}$ phosphane, sulfane, arene or alkene group or the 4,5-diarylimidazole derivative according to formula (I) and n of formula (III) is an integer of from 1 to 3. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a fluorine atom or a methoxy group, R2 is a $C_{1-4}$ alkyl group, M of formula (III) is a metal atom, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a $C_{1-4}$ alkyl group, M of formula (III) is a metal atom, L of formula (III) is a $P_{1-4}$ phosphane, sulfane, arene or alkene group or the 4,5-diarylimidazole derivative according to formula (I) and n of formula (III) is an integer of from 1 to 5. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a fluorine atom or a methoxy group, R2 is a $C_{1-4}$ alkyl group, M of formula (III) is Cu, Ag, Au, Rh, Ir, Pt or Ru, L of formula (III) is a $P_{1-4}$ phosphane, sulfane, arene or alkene group or the 4,5-diarylimidazole derivative according to formula (I) and n of formula (III) is an integer of from 1 to 3. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a fluorine atom or a methoxy group, R2 is a $C_{1-4}$ alkyl group, M of formula (III) is Cu, Ag, Au, Rh, Ir, Pt or Ru, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a fluorine atom or a methoxy group, R2 is a methyl or ethyl group, M of formula (III) is a metal atom, L of formula (III) is a $P_{1-4}$ phosphane, sulfane, arene or alkene group or the 4,5-diarylimidazole derivative according to formula (I) and n of formula (III) is an integer of from 1 to 5. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a fluorine atom or a methoxy group, R2 is a methyl or ethyl group, M of formula (III) is a metal atom, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a methyl or ethyl group, M of formula (III) is Cu, Ag, Au, Rh, Ir, Pt or Ru, L of formula (III) is a $P_{1-4}$ phosphane, sulfane, arene or alkene group or the 4,5-diarylimidazole derivative according to formula (I) and n of formula (III) is an integer of from 1 to 3. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a methyl or ethyl group, M of formula (III) is a metal atom, L of formula (III) is a $P_{1-4}$ phosphane, sulfane, arene or alkene group or the 4,5-diarylimidazole derivative according to formula (I) and n of formula (III) is an integer of from 1 to 5. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a methyl or ethyl group, M of formula (III) is a metal atom, L of formula (III) is a $P_{1-4}$ phosphane, sulfane, arene or alkene group or the 4,5-diarylimidazole derivative according to formula (I) and n of formula (III) is an integer of from 1 to 3. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a methyl or ethyl group, M of formula (III) is a metal atom, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a $C_{1-4}$ alkyl group, M is Cu, Ag, Au, Rh, Ir, Pt or Ru, L is the 4,5-diarylimidazole derivative according to formula (I) and n is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a fluorine atom or a methoxy group, R2 is a $C_{1-4}$ alkyl group, M of formula (III) is a metal atom, L of formula (III) is a $P_{1-4}$phosphane, sulfane, arene or alkene group or the 4,5-diarylimidazole derivative according to formula (I) and n of formula (III) is an integer of from 1 to 5. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a $C_{1-4}$ alkoxy group, R2 is a $C_{1-4}$ alkyl group, M of formula (III) is a transition metal atom, L of formula (III) is a $P_{1-4}$phosphane, sulfane, arene or alkene group or a 4,5-diarylimidazole derivative according to formula (I) and n of formula (III) is an integer of from 1 to 3. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a $C_{1-4}$ alkoxy group, R2 is a $C_{1-4}$ alkyl group, M of formula (III) is a metal atom, L of formula (III) is a $P_{1-4}$ phosphane, sulfane, arene or alkene group or a 4,5-diarylimidazole derivative according to formula (I) and n of formula (III) is an integer of from 1 to 5. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a $C_{1-4}$ alkoxy group, R2 is a $C_{1-4}$ alkyl group, M of formula (III) is a metal atom, L of formula (III) is a $P_{1-4}$ phosphane, sulfane, arene or alkene group or a 4,5-diarylimidazole derivative according to formula (I) and n of formula (III) is an integer of from 1 to 3. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a $C_{1-4}$ alkoxy group, R2 is a $C_{1-4}$ alkyl group, M of formula (III) is a metal atom, L of formula (III) is the 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a halogen atom or a methoxy or ethoxy group, R2 is a $C_{1-4}$ alkyl group, M of formula (III) is Cu, Ag, Au, Rh, Ir, Pt or Ru, L of formula (III) is a $P_{1-4}$ phosphane, sulfane, arene or alkene group or a 4,5-diarylimidazole derivative according to formula (I) and n of formula (III) is an integer of from 1 to 2. Preferably, the hydroxamic acid is at position 3 or 4 of the first aryl ring. Preferably, the R1 is in para (1,4) position of the second aryl ring of the 4,5-diarylimidazole derivative.

According to the invention, the 4,5-diarylimidazole derivatives are compounds of formulae (I), (II) or (III) or pharmaceutically acceptable salts thereof, wherein the 4,5-diarylimidazole derivatives have a hydroxamic acid residue at a first aryl ring and a residue R1 at a second aryl ring and wherein R1 is a hydrogen, a fluorine atom or a methoxy group, R2 is a methyl or ethyl group, M of formula (III) is Au, L of formula (III) is a 4,5-diarylimidazole derivative according to formula (I) and n of formula (III) is 1. Preferably, the hydroxamic acid is at position 3 or 4 of the first aryl ring. Preferably, the R1 is in para (1,4) position of the second aryl ring of the 4,5-diarylimidazole derivative.

Particular preferred 4,5-diarylimidazole derivatives have the formula (IV), (V), (VI), (VII), (VIII) and (IX):

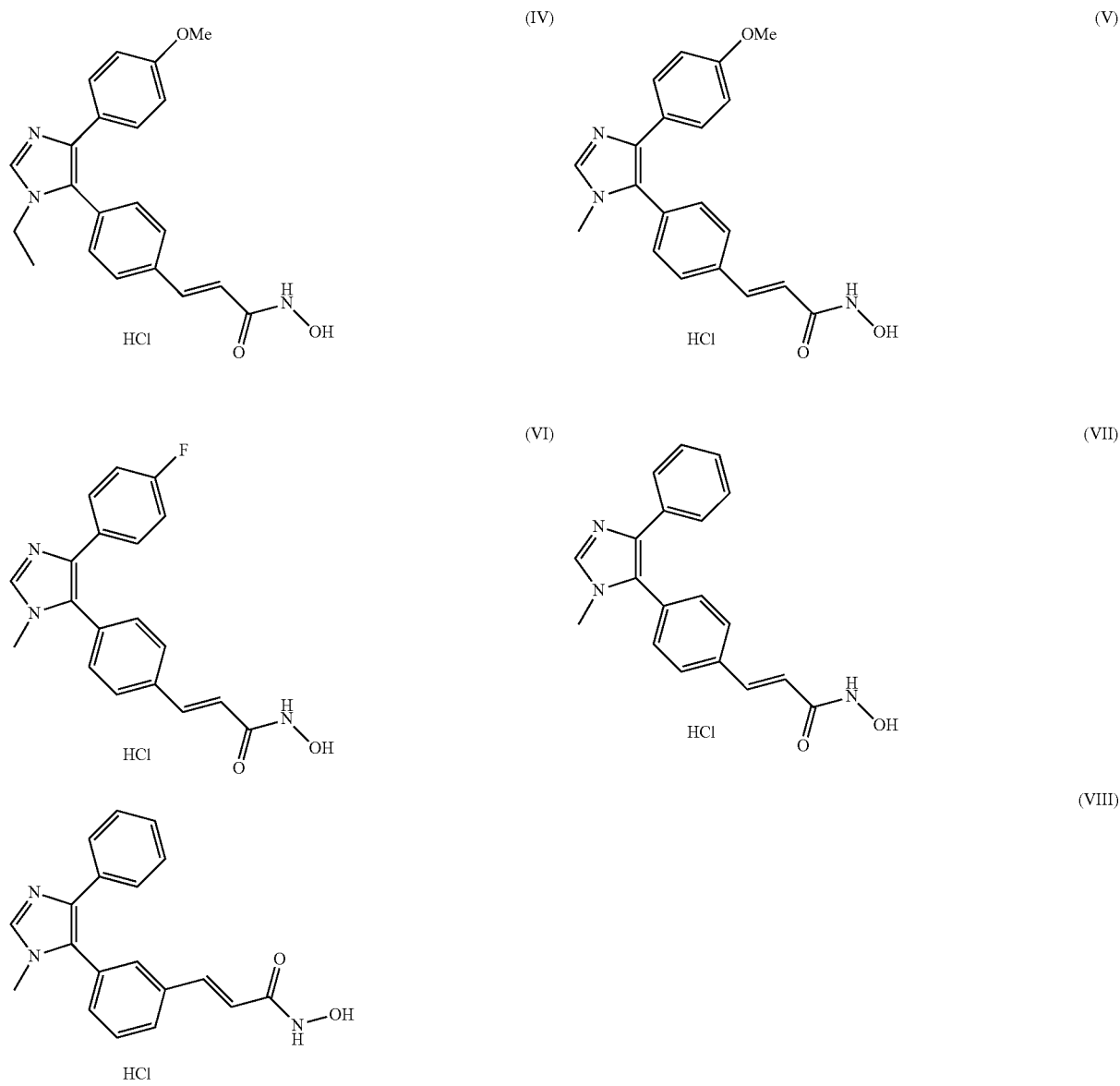

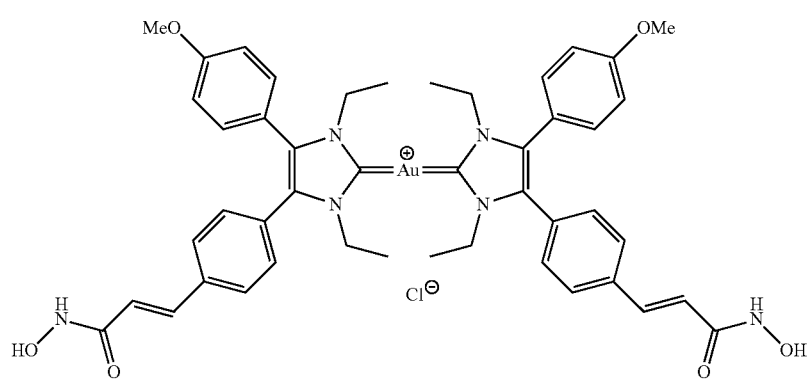

(IX)

The 4,5-diarylimidazole derivatives of the present invention can be synthesized by methods well known to the person skilled in the art. Exemplary synthesizing steps are as described in the following: In a first step, a toluenesulfonylmethyl isocyanide reagent ($CH_3C_6H_4SO_2CH_2NC$) is cyclized with 4-formyl-t-butylcinnamate, followed by a subsequent deprotection and reaction with THP-protected hydroxylamine which results in the formation of a THP-protected hydroxamate. The THP-protecting group is then removed e.g. under acidic conditions which results in a 4,5-diarylimidazole derivative. The THP-protected hydroxamate can also be used for the production of metal complexes of the 4,5-diarylimidazole derivatives. Alkylation of the THP-protected hydroxamate with an alkylhalogenide results in a imidazolium salt which can be transferred into a 4,5-diarylimidazole metal complex. Representative methods for synthesizing the 4,5-diarylimidazole derivatives of the present invention are provided in the examples.

The present invention also relates to 4,5-diarylimidazole derivatives for use in the treatment of diseases.

As used herein, the term "treating" encompasses to reversing, alleviating or inhibiting the progress of a disease, disorder or condition, or improvement of one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein the term "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

Examples of various diseases that may be treated using the 4,5-diarylimidazole derivatives of the present invention can be diseases involving undesirable or uncontrolled cell proliferation. Such indications include benign tumors, various types of cancers such as primary tumors and tumor metastasis, abnormal angiogenesis and parasitic diseases. More specific indications are colon cancer, breast cancer, cervix cancer, melanoma cancer, hepatoma, ovary cancer, prostate cancer, renal cancer, pancreatic cancer, stomach cancer, neuroendocrine cancer, testicular cancer, skin cancers other than melanoma cancer, head and neck cancer, bone cancer, lymphoma, leukemia, myeloma. Preferably, the cancer is colon cancer, breast cancer, cervix cancer or melanoma cancer.

Abnormal angiogenesis that may be treated using the 4,5-diarylimidazole derivatives of the present invention include those abnormal angiogenesis accompanying rheumatoid arthritis, ischemic-reperfusion related brain edema and injury, cortical ischemia, ovarian hyperplasia and hypervascularity, endometriosis, psoriasis, diabetic retinopathy, and other ocular angiogenic diseases such as retinopathy of prematurity, macular degeneration, corneal graft rejection, neuroscular glaucoma and Oster Webber syndrome. Preferably, the abnormal angiogenesis is macular degeneration, more preferably age-related macular degeneration.

Parasitic diseases that may be treated using the 4,5-diarylimidazole derivatives of the present invention are protozoan infections preferably leishmaniasis or trypanosomiasis.

Preferably, the 4,5-diarylimidazole derivatives of the present invention are used in the treatment of cancer.

The present invention also relates to the use of the 4,5-diarylimidazole derivatives for the manufacture of a medicament for the treatment of cancer, macular degeneration or protozoan infections. Preferably, of the 4,5-diarylimidazole derivatives are used for the manufacture of a medicament for the treatment of cancer, more preferably for the treatment of colon cancer, breast cancer, cervix cancer and melanoma cancer.

The present invention also relates to a pharmaceutical composition comprising as an active ingredient a 4,5-diarylimidazole derivative of the present invention. Such pharmaceutical compositions may comprise, in addition to the 4,5-diarylimidazole derivatives of the invention or their pharmaceutically acceptable salts, one or more pharmaceutically acceptable excipients. The term "excipient" is used herein to describe any ingredient other than the compound of the invention. The choice of excipient will to a large extent depend on the particular mode of administration. Excipients can e.g. be suitable carriers, retardants, boosters, prolonging substances, adjuvants, stabilizers, binders, emulsifiers, surface active agents, penetration enhancers suspending agents, disintegrants, buffers, salts, dilutents, solvents, dispersion media, fillers, lubricants, propellants, preservatives, flavours or mixtures thereof.

The present invention also relates to a method for treating cancer, wherein a patient in need of such therapy is administered a therapeutically effective dose of a 4,5-diarylimidazole derivative of the present invention or a pharmaceutically acceptable salt thereof. Preferably, the cancer is selected from colon cancer, breast cancer, cervix cancer, melanoma cancer.

The present invention is also directed to a method for treating cancer, wherein a patient in need of such therapy is administered a therapeutically effective dose of a pharmaceutical composition of the present invention. Preferably, the cancer is selected from colon cancer, breast cancer, cervix cancer, melanoma cancer.

The 4,5-diarylimidazole derivatives of the invention are administered preferably at an effective dose. An "effective dose" is the dose of a 4,5-diarylimidazole derivative that upon administration to a patient yields a measurable therapeutic effect with regard to the disease of interest. In the present invention an effective dose is the dose of a 4,5-diarylimidazole derivative that upon administration to a patient yields a therapeutic effect with regard to at least one disease related symptom in a patient or patients suffering from said disease. Preferably, the 4,5-diarylimidazole derivative of the invention is administered at a dose of not more than 500 mg/kg/d. In particular, the 4,5-diarylimidazole derivative can be administered at a dose of 1 mg/kg/d to 400 mg/kg/d, preferably of 20 mg/kg/d to 150 mg/kg/d. In any event, the physician or the skilled person will be able to determine the actual dose which will be suitable for an individual patient, which is likely to vary with the age, weight, sex, and concomitant illnesses such as renal or hepatic dysfunction and response of the particular patient to be treated. The above mentioned dosages are exemplary of the average case. There can, of course, be individual instances where higher or lower dosage ranges are appropriate, and such are within the scope of the invention.

The 4,5-diarylimidazole derivatives of the present invention are preferably administered orally, intravenously, subcutaneously, bucally, rectally, dermally, nasally, tracheally, bronchially or by any other parenteral route or via inhalation in a pharmaceutically acceptable dosage form.

The 4,5-diarylimidazole derivatives of the present invention may be administered orally. Oral administration may involve swallowing, so that the compound enters the gastrointestinal tract, or buccal or sublingual administration may be employed by which the compound enters the blood stream directly from the mouth.

Formulations suitable for oral administration include: solid formulations such as tablets; capsules containing particulates, liquids, or powders; lozenges (including liquid-filled); and chews; multi- and nano-particulates; gels; solid solutions; liposomes; films, ovules, sprays and liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

For tablet dosage forms, depending on dose, the compound may make up from 1 weight % to 80 weight % of the dosage form, more typically from 5 weight % to 60 weight % of the dosage form. In addition to the compound, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% compound, from about 10 weight % to about 90 weight % binder, from about 0 weight % to about 85 weight % diluent, from about 2 weight % to about 10 weight % disintegrant, and from about 0.25 weight % to about 10 weight % lubricant.

The 4,5-diarylimidazole derivatives of the present invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art.

The 4,5-diarylimidazole derivatives of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol.

The 4,5-diarylimidazole derivatives of the present invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin. The pressurised container, pump, spray, atomizer, or nebuliser contains a solution or suspension of the 4,5-diarylimidazole derivatives of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

The use of 4,5-diarylimidazole derivatives in the treatment of diseases, preferably of cancer, may have the advantage that such compounds may be more efficacious than, be less toxic than, be longer acting than, be more potent than, produce fewer side effects than, be more easily absorbable than, have better pharmacokinetic profile (e.g. higher oral bioavailability and/or lower clearance) than, and/or have other useful pharmacological, physical, or chemical properties over compounds known in the prior art for treatment of said diseases.

FIGURES

FIG. 1: Synthesis of the 4,5-diarylimidazole derivatives.

Figure 2:
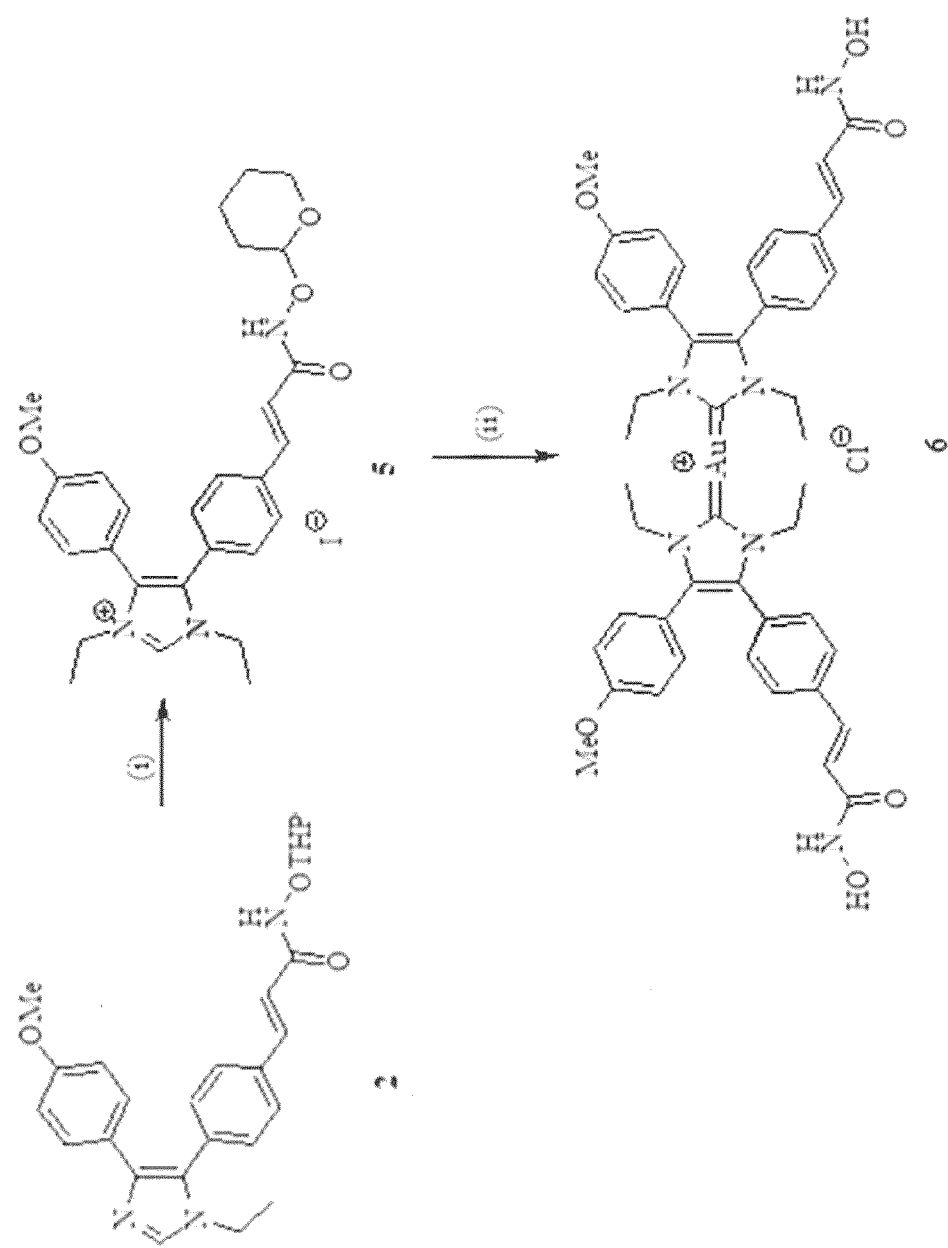

FIG. 2: Synthesis of the 4,5-diarylimidazole derivative metal complexes.

Figure 3:
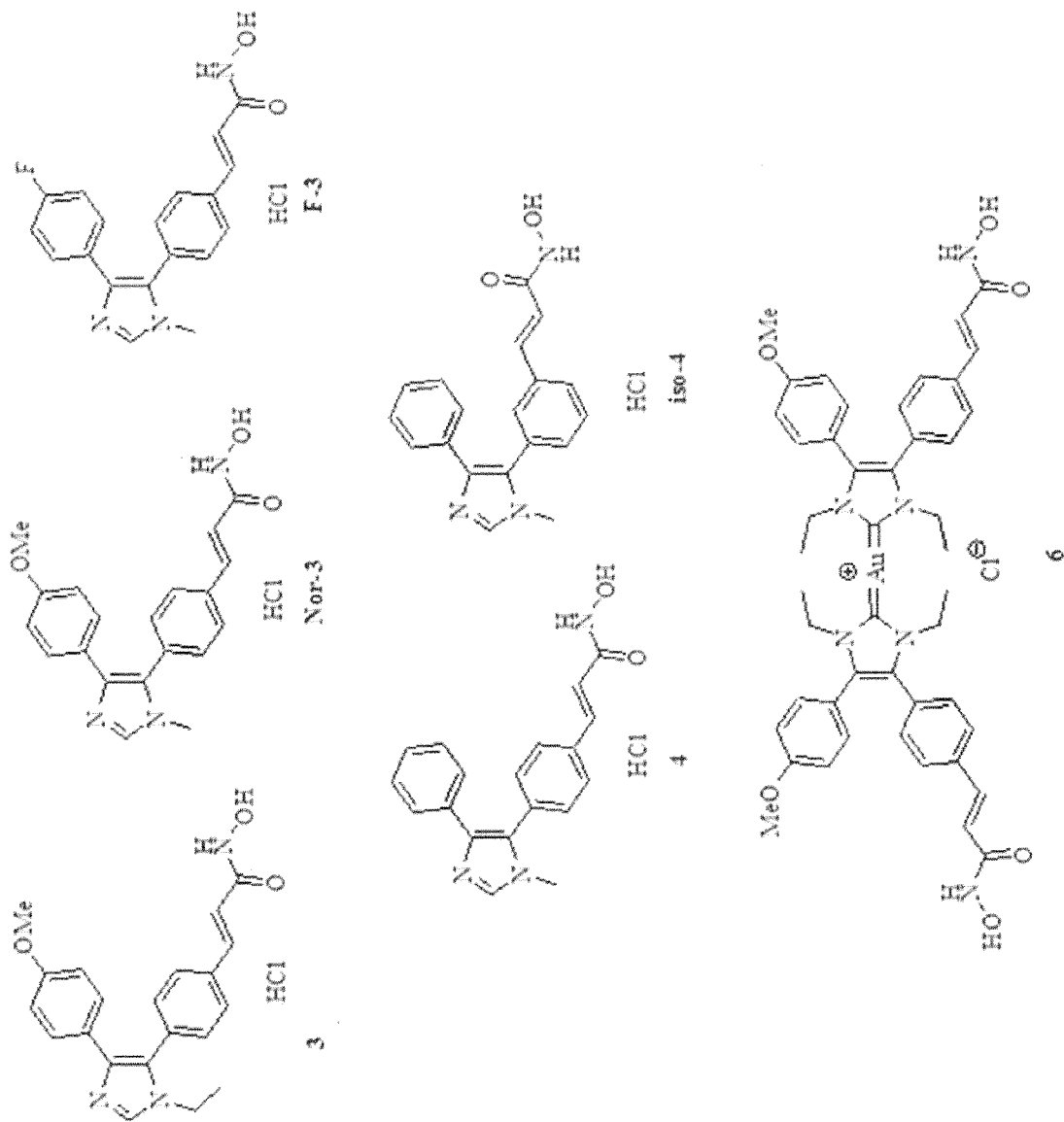

FIG. 3: Structures of exemplarily synthesized 4,5-diarylimidazole derivatives: compound 3 (Et-Animacroxam), its analogs Nor-3 and F-3, compound 4 (Bimacroxam) and its isomer iso-4, and the gold derivative (compound 6).

Figure 4:
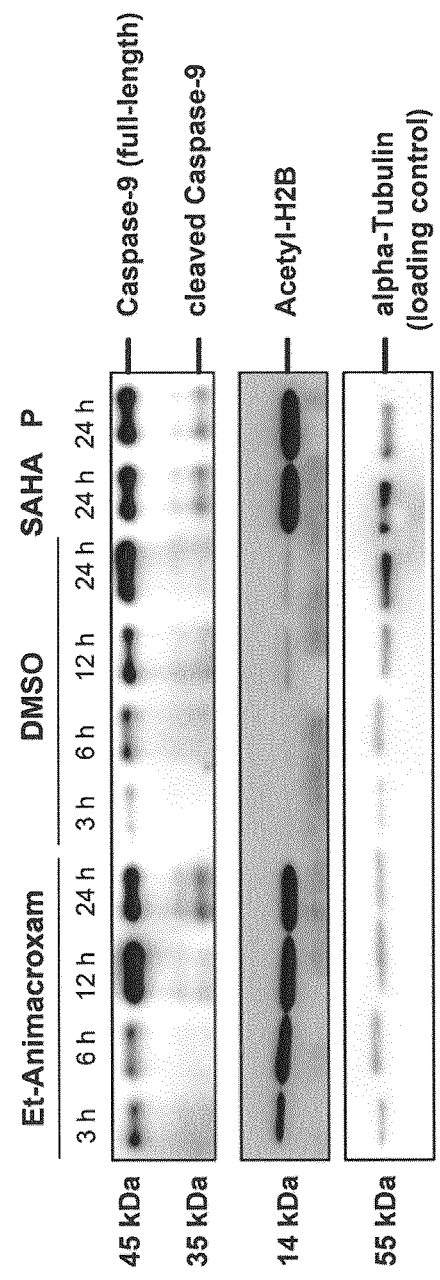

FIG. 4: Incubation of 518A2 melanoma cells with Et-Animacroxam leads to apoptosis induction (caspase-9-cleavage) and acetylation of histone H2B. Western blot analysis of 518A2 cell lysates after drug treatment (3-24 h). Control: DMSO; Positive control: SAHA, 5 µM, 24 h; P=Panobinostat, 5 µM, 24 h (pan-HDAC inhibitor).

Figure 5:
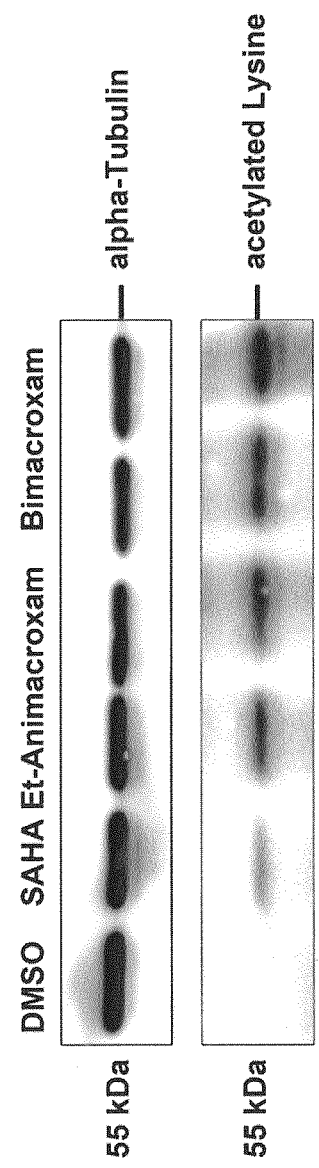

FIG. 5: Increase of acetylated microtubules in 518A2 melanoma cells after treatment with SAHA (5 µM, 24 h) or Et-Animacroxam and Bimacroxam (2.5 µM or 5 µM, 24 h). Cell lysates were subjected to gel electrophoresis and immunoblotting for acetylated lysine residues in alpha-tubulin (55 kDa).

Figure 6:
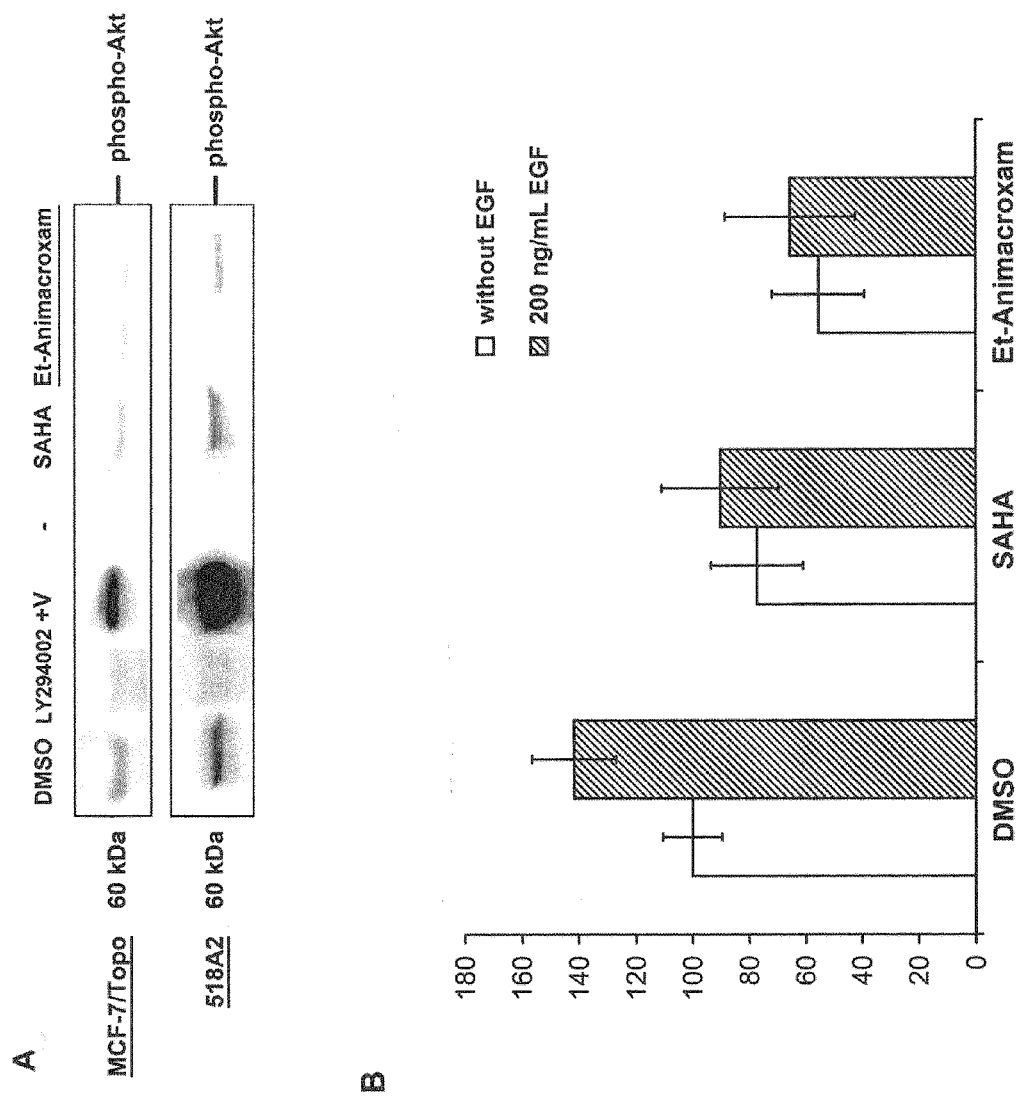

FIG. 6: Influence of imidazole-based HDAC inhibitors Et-Animacroxam (compound 3) and Bimacroxam (compound 4) on resistance factors in tumor cell lines. A: Western blot analysis of Akt-phosphorylation (phospho-Akt) in 518A2 and MCF-7/Topo cell lysates (10 µg protein each) after 6 h of incubation. PI3K inhibitor LY294002, 50 µM; SAHA, 5 µM; Et-Animacroxam, 5 µM and 2.5 µM. B: Matrigel-Transwell-Migration Assay with MCF-7/Topo breast cancer cells after EGF stimulation (200 ng/mL) and incubation with compounds for 48 h (5 µM SAHA, 2.5 µM Et-Animacroxam). The amount of invasive cells was determined after calcein treatment via fluorescence measurement and DMSO-treated controls without EGF were set to 100%.

Figure 7:
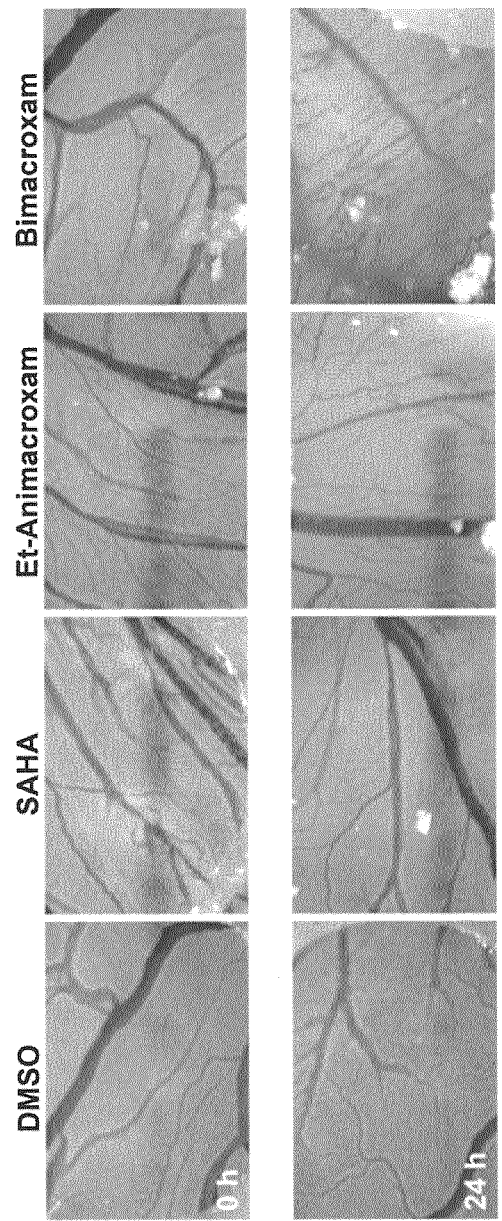

FIG. 7: CAM assay with fertilized chicken eggs directly after treatment (0 h) or after 24 h of incubation with 20 nmol SAHA (Vorinostat), Et-Animacroxam (compound 3) or Bimacroxam (compound 4). 60-fold magnification.

Figure 8:
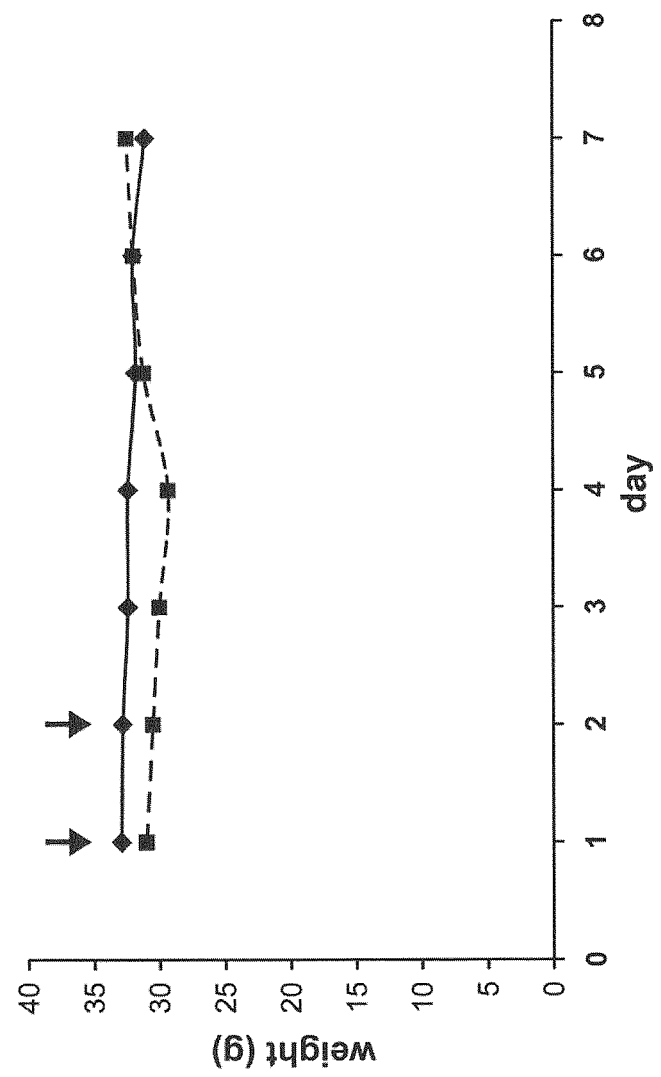

FIG. 8: Tolerance of Et-Animacroxam (compound 3) in two Balb/c mice (x-axis: day 1-7; y-axis: weight in gram). On days 1 and 2, 20 mg/kg (i.p.) of Et-Animacroxam were given and the mice were observed for a further 5 days.

Figure 9:
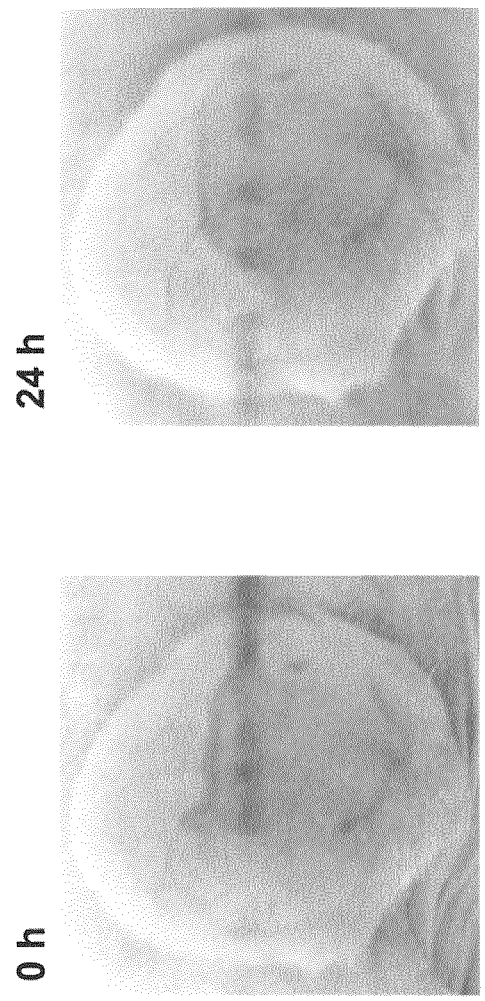

FIG. 9: Activity of Et-Animacroxam (compound 3) in the 1411HP xenograft model (left: before treatment; right: 24 h after treatment with 150 mg/kg i.p. of Et-Animacroxam).

EXAMPLES

In the present invention new N-alkyl-4,5-diarylimidazoles with prop-2-enoylhydroxamic acid residue at position 3 or 4 of the first aryl ring are described in formulae (I), (II) and (III). Additional substituents ($R^1$) like halogens (F, Cl, Br, I) and/or alkoxy groups, preferably methoxy groups, can be attached at the second aryl ring. At the imidazole nitrogen alkyl substituents ($R^2$) such as methyl, ethyl, etc., are attached. The present invention also encompasses the synthesis of new metal-carbene complexes derived from the above imidazoles and containing preferably the biologically active metal ions Cu(I), Ag(I), Au(I), Au(III), Rh(I), Ir(I), Pt(II), Pt(IV) and Ru(II), the latter preferably as ($\eta^6$-arene) Ru(II).

Structure and Synthesis of the Hydroxamic Acids Exemplified for Compound 3 (Et-Animacroxam) and a Gold-Carbene Complex 6.

4,5-diarylimidazole derivatives according to the present invention may be synthesized according to a variety of reaction schemes. Some synthesis protocols are provided herein in the examples. Other synthesis protocols could be readily devised by those skilled in the art. An exemplary protocol for the synthesis of the 4,5-diarylimidazole derivatives is shown in FIG. 1. Initially, THP-protected hydroxamate (compound 2) was obtained from a cyclization reaction of the TosMIC reagent (compound 1) with 4-formyl-t-butylcinnamate and subsequent deprotection and reaction with THP-protected hydroxylamine. Finally, the THP protecting group was removed under acidic conditions to give the target compound 3 (Et-Animacroxam) as a hydrochloride salt.

FIG. 2 illustrates the synthesis of the corresponding NHC-metal complexes (M=Cu, Ag, Au, Pt, Ru, Rh, Ir) which can be started exemplarily from the THP-protected derivative (compound 2). Alkylation of the imidazole with an alkylhalogenide, e.g., iodoethane, gives the imidazolium salt (compound 5), which is transferred to the gold carbene (compound 6) via the silver carbene intermediate after deprotection with HCl in dioxane.

Experimental and Analytical Data of the Tested Compounds

1-Ethyl-4-(4-methoxyphenyl)-5-(4'-tetrahydropyranyloxyaminocarbonylethenyl-phenyl)-imidazole
(Compound 2)

A mixture of 4-formyl-t-butylcinnamate (97 mg, 0.42 mmol) and 2M $EtNH_2$/THF (1.05 mL, 2.10 mmol) in t-butanol (15 mL) was refluxed for 2 h. After cooling down to room temperature compound 1 (126 mg, 0.42 mmol) and $K_2CO_3$ (500 mg, 3.62 mmol) were added and the reaction mixture was refluxed for 3 h. The solvent was evaporated in vacuum, the residue dissolved in ethyl acetate and washed with water and brine, dried over $Na_2SO_4$, filtered and concentrated in vacuum. The residue was purified by column chromatography (silica gel 60, ethyl acetate/MeOH 9:1) and 1-ethyl-4-(4-methoxyphenyl)-5-(4-tert-butoxycarbonylethenylphenyl)-imidazole was obtained as a yellow oil. Yield: 72 mg (0.18 mmol, 43%); $R_f$=0.73 (ethyl acetate/MeOH, 9:1); $v_{max}$ (ATR)/cm$^{-1}$: 2976, 2932, 2835, 1702, 1634, 1611, 1563, 1518, 1494, 1457, 1407, 1392, 1367, 1323, 1292, 1244, 1209, 1173, 1146, 1104, 1030, 981, 949, 871, 832, 799, 767, 730, 660; $^1$H NMR (300 MHz, CDCl$_3$): δ 1.23 (3 H, t, J=7.3 Hz), 1.51 (9 H, s), 3.71 (3 H, s), 3.7-3.9 (2 H, m), 6.39(1 H, d, J=16.0 Hz), 6.71 (2 H, d, J=9.0 Hz), 7.3-7.4 (4 H, m), 7.5-7.6 (4 H, m); $^{13}$C NMR (75.5 MHz, CDCl$_3$): δ 16.3, 28.1, 40.1, 55.0, 80.6, 113.7, 114.4, 120.9, 126.5, 127.1, 127.5, 127.9, 128.4, 131.0, 132.0, 132.5, 134.6, 135.5, 136.2, 138.5, 142.5, 158.2, 166.0. The obtained t-butyl ester (72 mg, 0.18 mmol) was dissolved in $CH_2Cl_2$ (3 mL), treated with TFA (2 mL) and stirred at room temperature for 1 h. The solvent was removed in vacuum, the residue dried in vacuum and used for the next step without further purification. The residue was dissolved in dry $CH_2Cl_2$ and EDCI (98 mg, 0.51 mmol), DMAP (19 mg, 0.14 mmol), triethylamine (117 µL, 0.55 mmol) and tetrahydropyranylhydroxylamine (71 mg, 0.61 mmol) were added. After stirring at room temperature for 24 h the solvent was removed in vacuum and the residue was purified by column chromatography (silica gel 60, ethyl acetate/MeOH, 9:1). Yield: 52 mg (0.12 mmol, 67%); $R_f$=0.37 (ethyl acetate/MeOH, 95:5); $v_{max}$ (ATR)/cm$^{-1}$: 3158, 2941, 2869, 1662, 1626, 1613, 1518, 1494, 1462, 1442, 1336, 1294, 1245, 1203, 1174, 1129, 1112, 1030, 981, 948, 895, 872, 831, 816, 800, 727, 661; $^1$H NMR (300 MHz, CDCl$_3$): δ 1.1-1.3 (3 H, m), 1.5-1.6 (3 H, m), 1.8-1.9 (3 H, m), 3.5-3.6 (1 H, m), 3.66 (3 H, s), 3.7-3.9 (2 H, m), 4.0-4.1 (1 H, m), 5.0-5.1 (1 H, m), 6.4-6.5 (1 H, m), 6.68 (2 H, d, J=8.9 Hz), 7.2-7.3 (2 H, m), 7.31 (2 H, d, J=8.9 Hz), 7.4-7.5 (1 H, m), 7.62 (1 H, s), 7.7-7.8 (1 H, m); $^{13}$C NMR (75.5 MHz, CDCl$_3$): δ 16.3, 18.6, 25.0, 28.1, 40.2, 55.1, 62.5, 102.5, 113.6, 126.6, 126.8, 128.0, 131.0, 132.1, 134.9, 136.2, 138.3, 158.3.

1-Ethyl-4-(4-methoxyphenyl)-5-(4'-hydroxyaminocarbonylethenyl-phenyl)-imidazole×HCl (Compound 3=Et-Animacroxam)

The THP-protected hydroxamate (compound 2) (52 mg, 0.12 mmol) was dissolved in $CH_2Cl_2$/MeOH (5 mL, 4:1) and treated with 4M HCl/dioxane (3 mL). The reaction mixture was stirred at room temperature for 1 h. The solvent was removed in vacuum and the residue was recrystallised from EtOH/n-hexane. Yield: 48 mg (0.12 mmol, 100%); colorless solid, mp.: 194-196° C.; $v_{max}$ (ATR)/cm$^{-1}$: 3126, 3000, 2970, 2833, 2765, 2626, 1653, 1603, 1571, 1540, 1510, 1462, 1427, 1412, 1349, 1299, 1258, 1181, 1113, 1085, 1053, 1027, 987, 828, 798, 766, 735, 692; $^1$H NMR (300 MHz, DMSO-d$_6$): δ 1.27 (3 H, t, J=7.3 Hz), 3.74 (3 H, s), 4.02 (2 H, q, J=7.3 Hz), 6.65 (1 H, d, J=15.9 Hz), 6.95 (2 H, d, J=9.0 Hz), 7.33 (2 H, d, J=9.0 Hz), 7.5-7.6 (3 H, m), 7.73 (2 H, d, J=8.2 Hz), 9.41 (1 H, s); $^{13}$C NMR (75.5 MHz, DMSO-d$_6$): δ 14.8, 42.3, 55.3, 114.4, 119.1, 121.2, 126.9, 127.8, 128.4, 128.8, 129.7, 131.5, 134.7, 136.6, 137.0, 159.8, 162.3; m/z (%) 363 (7) [M$^+$], 347 (100), 317 (41), 280 (18), 45 (21).

1-Methyl-4-(4-methoxyphenyl)-5-(4'-hydroxyaminocarbonylethenyl-phenyl)-imidazole×HCl (Compound Nor-3)

The corresponding THP-protected hydroxamate (44 mg, 0.11 mmol) was dissolved in $CH_2Cl_2$/MeOH (5 mL, 4:1) and 4M HCl/dioxane (3 mL) was added. The reaction mixture was stirred at room temperature for 1 h. The solvent was evaporated and the residue was crystallized from ethanol/n-hexane. Yield: 43 mg (0.11 mmol, 100%); off-white solid of mp 189° C.; IR (ATR): $v_{max}$ 3113, 3048, 2962, 2837, 2622, 1651, 1601, 1514, 1453, 1405, 1342, 1297, 1261, 1185, 1121, 1049, 1028, 998, 983, 872, 825, 799, 761, 735, 710 cm$^{-1}$; $^1$H NMR (300 MHz, DMSO-d$_6$): δ 3.56 (s, 3H), 3.75 (s, 3H), 6.60 (d, J=15.9 Hz, 1H), 6.96 (d, J=9.0 Hz, 2H), 7.31 (d, J=9.0 Hz, 2H), 7.5-7.6 (m, 3H), 7.73 (d, J=8.2 Hz, 2H), 9.32 (s, 1H); $^{13}$C NMR (75.5 MHz, DMSO-d$_6$): δ 34.2, 55.3, 66.4, 114.5, 119.2, 121.1, 126.7, 128.3, 128.9, 131.4, 135.7, 136.2, 160.0, 162.5; MS (EI) m/z 349 (5) [M$^+$], 334 (100), 321 (41), 303 (48), 288 (15), 277 (15), 44 (18).

1-Methyl-4-(4-fluorophenyl)-5-(4'-hydroxyaminocarbonylethenyl-phenyl)-imidazole×HCl (Compound F-3)

The corresponding THP-protected hydroxamate (46 mg, 0.12 mmol) was dissolved in $CH_2Cl_2$/MeOH (5 mL, 4:1) and 4M HCl/dioxane (3 mL) was added. The reaction mixture was stirred at room temperature for 1 h. The solvent was evaporated and the residue was crystallized from ethanol/n-hexane. Yield: 35 mg (0.094 mmol, 78%); off-white solid of mp 170° C.; IR (ATR): $v_{max}$ 3115, 3043, 2995, 2836, 2626, 1654, 1606, 1546, 1512, 1482, 1404, 1371, 1345, 1240, 1168, 1122, 1051, 1032, 1012, 998, 955, 937, 831, 763, 732, 711 cm$^{-1}$; $^1$H NMR (300 MHz, DMSO-d$_6$): δ 3.68 (s, 3H), 6.62 (d, J=15.9 Hz, 1H), 7.2-7.3 (m, 2H), 7.4-7.6 (m, 5H), 7.74 (d, J=8.1 Hz, 2H), 9.31 (s, 1H); $^{13}$C NMR (75.5 MHz, DMSO-d$_6$): δ 34.1, 109.5, 115.9, 116.2, 121.1, 123.8, 126.6, 128.3, 129.1, 129.3, 129.7, 129.8, 131.3, 136.2, 136.6, 137.0, 160.6, 162.3, 163.9; MS (EI) m/z (%) 337 (15) [M$^+$], 322 (32), 309 (37), 293 (100), 265 (24), 45 (39).

1-Methyl-4-phenyl-5-(4'-hydroxyaminocarbonylethenyl-phenyl)-imidazole×HCl (Compound 4=Bimacroxam)

The corresponding THP-protected hydroxamate (70 mg, 0.17 mmol) was dissolved in $CH_2Cl_2$/MeOH (5 mL, 4:1) and 4M HCl/dioxane (3 mL) was added. The reaction mixture was stirred at room temperature for 1 h. The solvent was evaporated and the residue was crystallized from ethanol/n-hexane. Yield: 50 mg (0.14 mmol, 82%); colorless solid of mp 189-190° C.; IR (ATR): $v_{max}$ 3142, 2992, 2826, 1655, 1607, 1525, 1500, 1446, 1403, 1345, 1166, 1118, 1050, 1032, 998, 957, 873, 834, 769, 723, 692 cm$^{-1}$; $^1$H NMR (300 MHz, DMSO-d$_6$): δ 3.68 (s, 3H), 6.63 (d, J=15.9 Hz, 1H), 7.3-7.4 (m, 5H), 7.5-7.6 (m, 3H), 7.74 (d, J=8.2 Hz, 2H), 9.37 (s, 1H), 10.9-11.0 (br s, 1H); $^{13}$C NMR (75.5 MHz, DMSO-d$_6$): (5 34.1, 121.2, 126.6, 127.1, 128.3, 129.0, 129.2, 129.3, 129.6, 131.3, 136.1, 136.6, 137.0, 162.2; MS (EI) m/z 319 (15) [M$^+$], 304 (100), 303 (86), 291 (76), 273 (48), 247 (48), 44 (37).

1-Methyl-4-phenyl-5-(3'-hydroxyaminocarbonylethenyl-phenyl)-imidazole×HCl (Compound iso-4)

The corresponding THP-protected hydroxamate (80 mg, 0.20 mmol) was dissolved in $CH_2Cl_2$/MeOH (5 mL, 4:1)

and 4M HCl/dioxane (3 mL) was added. The reaction mixture was stirred at room temperature for 1 h. The solvent was evaporated and the residue was crystallized from ethanol/n-hexane. Yield: 60 mg (0.17 mmol, 85%); off-white solid of mp 228° C.; IR (ATR): $v_{max}$ 3103, 3032, 2857, 2797, 1655, 1606, 1549, 1497, 1474, 1447, 1407, 1334, 1248, 1167, 1148, 1121, 1045, 995, 985, 971, 915, 801, 790, 768, 749, 719, 690, 667 cm$^{-1}$; $^1$H NMR (300 MHz, DMSO-d$_6$): δ 3.68 (s, 3H), 6.55 (d, J=15.9 Hz, 1H), 7.3-7.4 (m, 5H), 7.4-7.5 (m, 2H), 7.60 (t, J=7.8 Hz, 1H), 7.72 (s, 1H), 7.78 (d, J=7.8 Hz, 1H), 9.35 (s, 1H); $^{13}$C NMR (75.5 MHz, DMSO-d$_6$): δ 34.1, 111.5, 120.7, 126.8, 127.1, 127.3, 128.8, 129.0, 129.2, 129.7, 130.0, 131.6, 136.0, 137.1, 162.3; MS (EI) m/z 319 (23) [M$^+$], 303 (86). 275 (100), 257 (45), 232 (35), 204 (37), 189 (48).

Diethylimidazolium Salt (Compound 5)

THP-protected ethyl-animacroxam (37 mg, 0.083 mmol) was dissolved in acetonitrile (10 mL) and iodoethane (2 mL) was added. The reaction mixture was stirred at 85° C. for 24 h. The solvent was evaporated and the residue was dried in vacuum. Yield: 49 mg (0.081 mmol, 98%); yellow gum; $v_{max}$/cm$^{-1}$: 3131, 2940, 2849, 1710, 1664, 1626, 1557, 1522, 1506, 1454, 1386, 1353, 1340, 1294, 1251, 1203, 1177, 1129, 1112, 1022, 982, 945, 917, 872, 835, 806, 725; $^1$H NMR (300 MHz, CDCl$_3$): δ 1.4-1.6 (9 H, m), 1.7-1.9 (3 H, m), 3.6-3.7 (1 H, m), 3.76 (3 H, s), 4.0-4.1 (1 H, m), 4.2-4.3 (4 H, m), 5.0-5.1 (1 H, m), 6.8-6.9 (2 H, m), 7.1-7.3 (8 H, m), 7.4-7.5 (2 H, m), 10.11 (1 H, s).

Gold Complex (Compound 6)

Iodide salt 5 (49 mg, 0.081 mmol) was dissolved in CH$_2$Cl$_2$/MeOH (1:1, 30 mL) and Ag$_2$O (23 mg, 0.099 mmol) was added. The reaction mixture was stirred in the dark at room temperature for 5 h. Chloro(dimethylsulfide) gold(I) (15 mg, 0.051 mmol) was added and the reaction mixture stirred for additional 20 h. The suspension was filtered, the filtrate was dissolved in CH$_2$Cl$_2$/MeOH (5 mL, 4:1) and treated with 4M HCl/dioxane (3 mL) and stirred at room temperature for 1 h. The solvent was evaporated and the residue recrystallised from ethanol/n-hexane. Yield: 40 mg (0.039 mmol, 47%); yellow solid of mp 120-122° C.; $v_{max}$/cm$^{-1}$: 2952, 2929, 2849, 1716, 1661, 1627, 1609, 1573, 1518, 1504, 1460, 1409, 1377, 1345, 1314, 1291, 1249, 1203, 1174, 1109, 1086, 1023, 979, 835, 812, 794; $^1$H NMR (300 MHz, DMF-d$_7$): δ 1.29 (6 H, t, J=7.2 Hz), 1.48(6 H, t, J=7.2 Hz), 3.7-3.9 (6 H, m), 4.1-4.4(8 H, q, J=7.2 Hz), 6.7-6.8 (2 H, m), 7.0-7.1 (4 H, m), 7.4-7.9 (14 H, m); $^{13}$C NMR (75.5 MHz, DMF-d$_7$): δ 15.5, 17.2, 44.4, 44.6, 55.3, 55.4, 114.5, 114.6, 119.6, 119.7, 119.9, 128.1, 128.9, 129.0, 130.3, 130.8, 131.6, 131.7, 132.8, 135.5, 136.5, 137.5, 143.8, 160.7, 160.9, 167.0, 168.6, 182.5.

Selected Results from Biological Assays

Table 1 shows that compound 3 (Et-Animacroxam) and 4 (Bimacroxam) displayed selective growth inhibitory activity in human BRAF-mutant 518A2 melanoma cells and resistant colon cancer, breast cancer, and cervix carcinoma cell lines at clinically relevant concentrations. Although generally less potent than compound 3 and compound 4 their analogs Nor-3, F-3 and iso-4 also displayed significant activity in 518A2 and HT-29 cancer cells. Compound 3 generally performed better compared with the approved HDAC inhibitor vorinostat/SAHA. However, compound 4 acts more selectively on endothelial cells (Ea.hy926 and HUVEC) compared with 3 and SAHA (12-fold stronger in primary endothelial cells and 10-fold stronger in the Ea.hy926 cell line). Only in the case of endothelial HUVEC Nor-3 is more active than 3. The high selectivity towards cancer cells is conserved in the new compounds as to results from chicken heart fibroblasts. Initial MTT assays with the gold carbene derivative 6 showed its distinctly stronger activity in 518A2 melanoma and HT-29 colon cancer cells (cancer cells of solid tumors) compared with that of the ligand analog 3.

TABLE 1

IC$_{50}$ values (μM, 72 h) of SAHA and hydroxamates 3, Nor-3, F-3, 4, iso-4 and gold complex 6 in tumor and endothelial cell lines. BRAF-mutant melanoma (518A2) and resistant colon (HT-29), breast (MCF-7/Topo), cervix (KB-V1/Vbl) cell lines, hybrid endothelial cells (Ea.hy926) as well as primary endothelial cells (HUVEC, human umbilical vein endothelial cells) and non-malignant fibroblasts (CF, chicken fibroblasts). n.d. = not determined.

| Cell line - Compound | 518A2 | HT-29 | MCF-7/Topo | KB-V1/Vbl | Ea.hy926 | HUVEC | CF |
|---|---|---|---|---|---|---|---|
| 3 | 0.95 ± 0.19 | 0.45 ± 0.03 | 5.60 ± 0.33 | 2.91 ± 0.98 | 0.99 ± 0.13 | 1.26 ± 0.45 | >50 |
| Nor-3 | 1.45 ± 0.07 | 0.71 ± 0.06 | n.d. | n.d. | n.d. | 0.83 ± 0.26 | n.d. |
| F-3 | 1.94 ± 0.04 | 1.45 ± 0.06 | n.d. | n.d. | n.d. | n.d. | n.d. |
| 4 | 2.76 ± 0.62 | 1.33 ± 0.07 | 15.31 ± 1.4 | 5.04 ± 1.82 | 0.16 ± 0.03 | 0.55 ± 0.29 | >50 |
| iso-4 | 2.23 ± 0.06 | 2.80 ± 0.07 | n.d. | n.d. | n.d. | n.d. | n.d. |
| 6 | 0.50 ± 0.04 | 0.30 ± 0.04 | n.d. | n.d. | n.d. | n.d. | n.d. |
| SAHA | 1.52 ± 0.07 | 0.73 ± 0.08 | 13.44 ± 0.7 | 7.89 ± 0.91 | 1.82 ± 0.18 | 7.62 ± 0.09 | >50 |

The compounds 3 and 4 are pan-HDAC inhibitors which inhibit a panel of HDAC enzymes (FIG. 4). Both nucleus-located HDACs (e.g., HDAC1 and HDAC8) predominantly catalysing the deacetylation of DNA-associated histones and cytoplasmic HDACs like HDAC6, which preferably targets alpha-tubulin units of the microtubules, are among them. FIG. 4 and FIG. 5 show for compounds 3 and 4 that after drug treatment both histone proteins (H2B) and alpha-tubulin are vastly acetylated. In the case of compounds 3 and 4 acetylated alpha-tubulin occurs to much higher extent compared with cells treated with SAHA. A higher cellular concentration of acetylated alpha-tubulin was also observed at lower doses of 3 and 4 compared with SAHA. Thus, compounds 3 and 4 inhibit the microtubule-associated HDAC6 more efficiently than SAHA. The inhibition of HDAC6 plays an important role and interferes with cellular transport processes via acetylation of tubulin, but also influences cell survival via acetylation of the important chaperone Hsp90, which subsequently undergoes ubiquitination and degradation in the proteasome. In addition, DNAdouble-strand breaks appear after HDAC6 inhibition and sensitization of transformed cells towards classical anticancer drugs like taxol and doxorubicin was observed.

The new compounds also inhibit the phosphorylation and activation of protein kinase B (Akt) more pronounced than vorinostat/SAHA as shown by Western blot analyses. A connection with the indirectly proved stronger inhibition of HDAC6 is conceivable, since Akt is a client protein of the HDAC6 target Hsp90 which is regulated by Akt signaling itself. Activated Akt signaling is connected with the development of resistance and cell growth/migration (EGFR/PI3K/Akt signaling), and it plays an important role in angiogenesis (VEGFR/Akt/ERK signaling). Akt-phosphorylation in 518A2 melanoma cells and MCF-7/Topo-breast cancer cells was suppressed efficiently after treatment for 6 h (FIG. 6A). A reduced cellular concentration of phospho-Akt could be the reason for the high efficacy of 3 in the Matrigel™-based transwell-migration-assay with EGF-stimulated MCF-7/Topo cells. This assay serves as a model of the invasiveness of tumor cells. MCF-7/Topo cells obviously display a significantly reduced invasiveness after exposition to 3 for two days (FIG. 6B). In addition the new compounds exhibited anti-angiogenic effects in the CAM assay, an in vivo model using fertilised chicken eggs (chorio allantoic membrane, CAM assay, FIG. 7).

FIG. 8 illustrates that two Balb/c mice showed no signs of toxicity after treatment with doses of 2×20 mg/kg (i.p.) of compound 3 on two consecutive days. The weight of both treated mice roughly remained the same, one of the two mice even gained in weight (FIG. 8 right). The low toxicity of compound 3 can be explained by the imidazole fragment of the compound, since in our earlier studies similar imidazole-bridged tubulin polymerisation inhibitors were also tolerated well by animals, also in comparison with other heterocycles such as oxazoles.

FIG. 9 shows distinct changes in the tumor blood vessel system of a 1411HP xenograft (1411HP=Cisplatin-resistant testicular cancer) after treatment with 150 mg/kg (i.p.) of compound 3. Already after 24 h the diameter of some bigger vessels of the tumor body was reduced significantly. This relatively high dose of 150 mg/kg did not cause any visible side effects in the mouse, thus, a complication-free treatment with higher doses should be conceivable.

Isolation of HDAC Active Cell Lysate Fractions and Preparation of Recombinant HDAC Isoforms Cell lysate fractions from HeLa cells were obtained by a modified protocol for nuclei preparation by Dignam et al., *Nucleic Acids Res.* 11, 1475-1489 (1983). Briefly, cell pellets from mass cultures were resuspended and incubated in cell extraction buffer (20 mM HEPES, 10 mM KCl, 0.1 mM EDTA, 0.1 mM EGTA, 1.5 mM MgCl2, 0.5 mM DTT) containing 0.1% Triton X-100 to lyse cell membranes and leave intact nuclei. After centrifugation (3,000 g, 2 min), the supernatant containing cytosolic proteins was aspirated from the nuclei pellet and the protein concentration of the cytosolic fraction was determined by a standard Bradford assay (Pierce/Thermo Scientific). The human HDAC1 gene was amplified from a HeLa cDNA library (HDAC1 sequence from human cDNA, Genbank accession no. NM04964; Sigma Aldrich). Hek-293 cells were transfected with the resulting plasmid construct (pCS2-GST-TEV3-hHDAC1). Recombinant GST-HDAC1 (glutathione S-transferase) fusion protein were concentrated from Hek-293 mass culture lysates (20 mM Tris-HCl, 100 mM NaCl, 10 mM NaF, 20 mM beta-glycerophosphate, 0.1% Triton X-100, pH 7.7) and GST affinity tag pulldown according to manufacturer's conditions (glutathione agarose beads, Pierce/Thermo Scientific). Glutathione (GSH)-beads were repeatedly washed (50 mM Tris-HCl, pH 8.0) and eluted with 50 mM Tris-HCl, 50 mM reduced GSH. Eluates were concentrated and buffer exchanged (50 mM Tris-HCl, pH 8.0) by centrifugal filter columns according to manufacturer's manual (Amicon Ultra-0.5 mL Centrifugal Filters, 10K device, Merck Millipore). The protein concentration of the final HDAC1 protein solution was determined by a standard Bradford assay (Pierce/Thermo Scientific; 0.21 mg/mL total protein).

HDAC Activity Assay

A fluorescence-based HDAC activity assay was used to assess the compound specificity for distinct HDAC classes. Visualisation of HDAC activity was achieved by using short acetylated peptide substrates coupled to a precursor fluorophore which was released by trypsin cleavage only upon previous deacetylation. The Fluor-de-Lys substrate used allows to measure broad-spectrum HDAC activity from extracts or recombinant protein. Herein, cell lysate fractions (HeLa nuclear and cytosolic extracts) or recombinant human HDAC1 and HDAC6 (HDAC1 (GST-tag) isolated from transfected Hek-293 mass cultures; HDAC6 (His-tag), Enzo Life Sciences) were incubated with vorinostat or the compounds 4 or 3 and the Fluor-de-Lys substrate (Fluor-de-Lys®-Green substrate, Enzo Life Sciences) according to manufacturer's conditions. A commercially available nuclear extract from Hela cells (HeLa nuclear extract, 2.0 mg/mL, Merck Millipore) was used as a reference without further evaluation. In brief, each sample (50 µL) containing 5 µL predilution of the test compounds (dilution series ranging from 100 µM to 100 nM), 20 µL protein dilution (0.5 µg HeLa nuclear extract, 1 µg HeLa cytosolic extract, 0.4 µg HDAC1, 0.2 µg HDAC6) and 25 µL of 50 µM or 100 µM Fluor-de-Lys substrate (final concentration of 25 µM for lysate fractions or 50 µM for HDAC6; all in HDAC assay buffer: 50 mM Tris-HCl, 137 mM NaCl, 2.7 mM KCl, 1 mM MgCl2, pH 8.0) were incubated in the wells of a black 96-well plate (half-area 96-well plate, µClear®, black, medium binding, greiner bio-one) at 37° C. for 60 min. The amount of deacetylated substrate was then visualised by adding 50 µL 1× developer (0.5 mg/mL trypsin, 0.1 mM EDTA, 0.1 mM vorinostat in 50 mM Tris-HCl, pH 7.4) and subsequent incubation at 37° C. for 10 min. The fluorescence intensity of the degraded HDAC substrate was measured with a microplate reader (Tecan) at an emission wavelength of 535 nm (excitation at 485 nm). All experiments were conducted in duplicates, blank and solvent (DMSO) controls were treated identically. The fluorescence intensity represents the relative HDAC activity within a sample with respect to DMSO controls set to 100%. $IC_{50}$ values from dose-response curves were calculated as the mean of at least two independent experiments±S.D.

To clarify this, the inhibitory effect of compounds 4 and 3 in vitro on recombinant HDAC1 and HDAC6 proteins as representatives for typical class I and class II HDAC isoforms was measured by a fluorometric assay. Vorinostat displayed the lowest $IC_{50}$ value (ca. 10 nM) for the inhibition of HDAC1 while Bimacroxam 4 (ca. twofold) and Et-Animacroxam 3 (ca. tenfold) were significantly less efficacious (Table 2).

Probably as a consequence of its reduced affinity for HDAC1, Et-Animacroxam 3 inhibited HDAC6 much better ($IC_{50}$: 66 nM) and more specifically than vorinostat ($IC_{50}$: 154 nM). Tubastatin A, a selective HDAC6 inhibitor displayed $IC_{50}$ values in a similar range. We also tested the HDAC inhibitory effect on HeLa nuclear and cytosolic cell lysate fractions which may contain a specific set of HDAC isoforms. Class I as well as class II HDAC were shown to shuttle between the cytoplasm and the nucleus with a typical equilibrium distribution. HDAC1 and HDAC2 (class I) for instance were predominantly found in nuclei, while HDAC3 can be cytoplasm membrane-associated and HDAC8 is essentially in the cytoplasm taking part in the regulation of actin-mediated cell contractility. In contrast, class IIb HDAC6 localises exclusively in the cytotoplasm.

TABLE 2

HDAC inhibition [IC$_{50}$ (μM)]a by vorinostat and the compounds 4 (Bimacroxam) and 3 (Et-Animacroxam) as determined by the conversion of HDAC substrate to fluorophores. HDAC active isolates from nuclei or cytosolic fractions of HeLa cell lysates or recombinant HDAC1 and HDAC6 were incubated with the HDAC substrate and analysed by fluorescence measurements.

| HDAC isoforms | compounds | | | |
|---|---|---|---|---|
| | Vorinostat | 4 | 3 | Tubastatin A |
| HeLa nuclear extract [a] | 0.231 ± 0.036 [b] | 0.234 ± 0.011 [b] | 0.504 ± 0.024 | n.d. |
| HeLa cytosolic extract [a] | 0.147 ± 0.023 | 0.132 ± 0.014 | 0.036 ± 0.014 | n.d. |
| HDAC1 [a] | 0.010 ± 0.003 | 0.028 ± 0.011 | 0.187 ± 0.037 | >1 |
| HDAC6 [a] | 0.154 ± 0.071 | 0.107 ± 0.023 | 0.066 ± 0.017 | 0.087 ± 0.038 |

[a] IC$_{50}$ values derived from dose-response curves obtained by measuring the percentage of deacetylated, fluorogenic substrate (25 μM Fluor-de-Lys substrate) relative to DMSO controls. HeLa nuclear extract: 0.5 μg; HeLa cytosolic extract: 1 μg; HDAC1 0.4 μg, HDAC6: 0.2 μg. Commercially available HeLa nuclear extract was used as a reference. Incubation time 60 min.
[b] Values from "Mahal et al. Cancer Chemother. Pharmacol. 75, 691-700, 2015";
n.d. not determined.

HeLa nuclear and cytoplasmic extracts contain a variety of HDAC isoforms and the IC$_{50}$ values for their inhibition by vorinostat and Et-Animacroxam 3 showed a tendency similar to that observed in the tests with the recombinant enzymes (Table 2). Et-Animacroxam was ca. 14 times more HDAC inhibiting in the cytosolic than in the nuclear fraction and ca. four times more active than vorinostat. The latter was only 2.5 times more active in the cytosolic extract when compared with the nuclear fraction. We assume that the imidazoles are specific to a certain degree for HDAC6 or other cytoplasmic HDAC and thus they might also influence HDAC6-related cellular events more markedly than vorinostat.

The invention claimed is:

1. A 4,5-diarylimidazole derivative of formulae (I), (II) or (III):

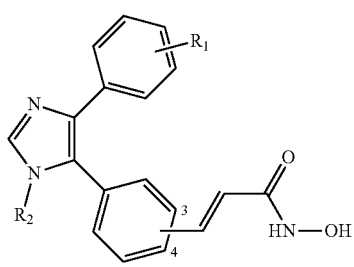

(I)

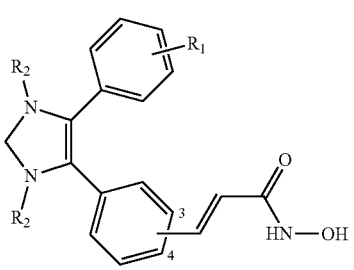

(II)

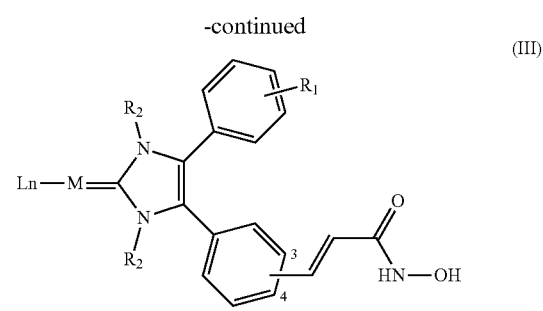

(III)

or a pharmaceutically acceptable salt thereof,
wherein the 4,5-diarylimidazole derivative has a hydroxamic acid residue at a first aryl ring and a residue R1 at a second aryl ring; and wherein
R1 is hydrogen, a halogen atom or an unsubstituted or substituted alkoxy group;
R2 is independently selected from an unsubstituted or substituted alkyl, alkoxy or alkene group;
M is a metal atom;
L is a halogen atom, an unsubstituted or substituted phosphane, sulfane, arene or alkene group or a 4,5-diarylimidazole-derivative of formula (I); and n is an integer of from 1 to 5.

2. The 4,5-diarylimidazole derivative according to claim 1, wherein R1 is a hydrogen, a halogen atom or a C$_{1-4}$ alkoxy group; preferably R1 is a hydrogen, a halogen atom or a methoxy or ethoxy group; more preferably R1 is a hydrogen, a fluorine atom or a methoxy group; most preferably R1 is a hydrogen or a methoxy group.

3. The 4,5-diarylimidazole derivative according to claim 1, wherein R2 is a C$_{1-4}$ alkyl group, preferably R2 is a methyl or ethyl group.

4. The 4,5-diarylimidazole derivative according to claim 1, wherein M is a transition metal atom, preferably M is Cu, Ag, Au, Rh, Ir, Pt or Ru, more preferably M is Au.

5. The 4,5-diarylimidazole derivative according to claim 1, wherein L is a P$_{1-}$ phosphane, sulfane, arene or alkene group or the 4,5-diarylimidazole derivative according to formula (I); preferably L is the 4,5-diarylimidazole derivative according to formula (I).

6. The 4,5-diarylimidazole derivative according to claim 1, wherein n is an integer of from 1 to 3, preferably n is an integer of from 1 to 2, more preferably n is 1.

7. The 4,5-diarylimidazole derivative according to claim 1, wherein the hydroxamic acid is at position 3 or 4 of the first aryl ring.

8. The 4,5-diarylimidazole derivative according to claim 1, wherein R1 is in para (1, 4) position of the second aryl ring.

9. The 4,5-diarylimidazole derivative according to claim 1, wherein the 4,5-diarylimidazole derivative has the formula (IV), (V), (VI), (VII), (VIII), or (IX):

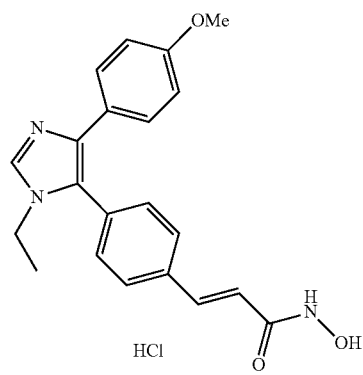

(IV)

(V)

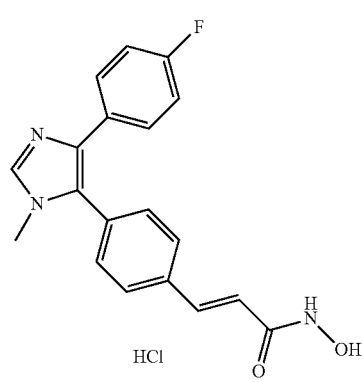

(VI)

(VII)

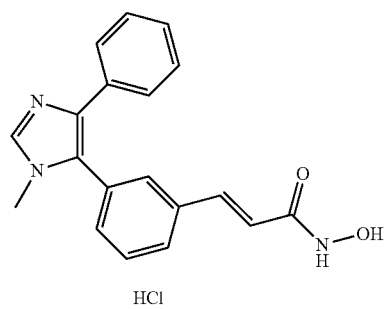

(VIII)

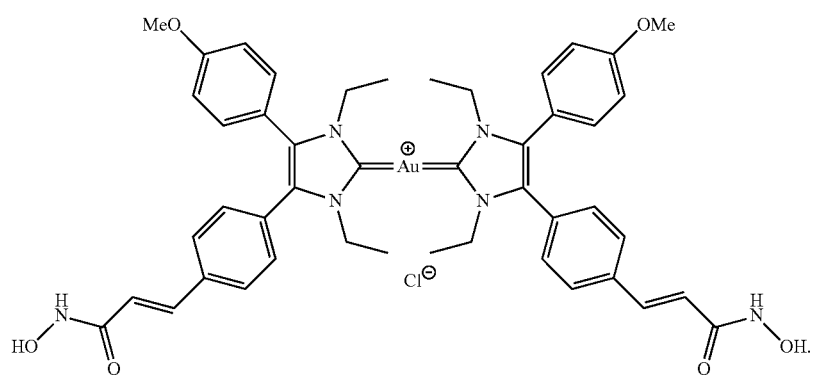

(IX)

10. A pharmaceutical composition comprising as an active ingredient a 4,5-diarylimidazole derivative according to claim 1.

11. The 4,5-diarylimidazole derivative according to claim 1 for use in the treatment of cancer, macular degeneration or protozoan infections, wherein the cancer is colon cancer, breast cancer, cervix cancer or melanoma cancer.

* * * * *